United States Patent
Bzdusek et al.

(10) Patent No.: US 9,600,856 B2
(45) Date of Patent: Mar. 21, 2017

(54) HYBRID POINT-BASED REGISTRATION

(75) Inventors: Karl Antonin Bzdusek, Madison, WI (US); Stephane Allaire, Nanterre (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 309 days.

(21) Appl. No.: 14/124,805

(22) PCT Filed: Jun. 4, 2012

(86) PCT No.: PCT/IB2012/052802
§ 371 (c)(1),
(2), (4) Date: Dec. 9, 2013

(87) PCT Pub. No.: WO2012/172454
PCT Pub. Date: Dec. 20, 2012

(65) Prior Publication Data
US 2014/0122112 A1    May 1, 2014

Related U.S. Application Data

(60) Provisional application No. 61/497,546, filed on Jun. 16, 2011.

(51) Int. Cl.
*G06T 3/00*    (2006.01)
*G06T 7/00*    (2006.01)
(Continued)

(52) U.S. Cl.
CPC .......... *G06T 3/0068* (2013.01); *G06F 19/321* (2013.01); *G06T 7/0012* (2013.01);
(Continued)

(58) Field of Classification Search
CPC ................ A61B 19/5244; A61B 19/50; A61B 2019/507; A61B 2019/5289;
(Continued)

(56) References Cited

U.S. PATENT DOCUMENTS

2005/0111757 A1 * 5/2005 Brackett ................ A61B 6/463
382/294
2006/0269165 A1    11/2006 Viswanathan
(Continued)

FOREIGN PATENT DOCUMENTS

WO    2006054194 A2    5/2006
WO    2006134565 A2    12/2006
(Continued)

OTHER PUBLICATIONS

Maurer Jr, Calvin R., et al. "Registration of 3-D images using weighted geometrical features." Medical Imaging, IEEE Transactions on 15.6 (1996): 836-849.*

(Continued)

*Primary Examiner* — Elaine Gort
*Assistant Examiner* — Jonathan Durant

(57) ABSTRACT

A system (28, 32) generates an image registration map. The system (28, 32) includes one or more processors (32) which receive a first image and a second image. Corresponding interest points in the first image and the second image are identified. Corresponding structures in the first and second images are identified and corresponding boundary points are identified on their boundaries. A registration map is generated from pairs of the corresponding interest points and a subset of pairs of the corresponding boundary points. The registration map is applied to one of the first and second images to register the one image to the other and propagate objects of interest over.

19 Claims, 2 Drawing Sheets

(51) Int. Cl.
  *G06F 19/00*  (2011.01)
  *A61N 5/10*  (2006.01)
(52) U.S. Cl.
  CPC .......... *G06T 7/0024* (2013.01); *G06T 7/0028* (2013.01); *G06T 7/0032* (2013.01); *G06T 7/0038* (2013.01); *A61N 5/1038* (2013.01); *G06T 2207/10072* (2013.01); *G06T 2207/20221* (2013.01)
(58) Field of Classification Search
  CPC ......... G06T 2207/20221; G06T 3/0068; G06T 7/0024; G06T 7/0038; A61N 5/1039
  See application file for complete search history.

(56) References Cited

U.S. PATENT DOCUMENTS

| | | | | |
|---|---|---|---|---|
| 2007/0223794 | A1* | 9/2007 | Preiss | A61B 8/12 382/128 |
| 2008/0205719 | A1* | 8/2008 | Pekar | G06T 3/0081 382/128 |
| 2009/0087124 | A1 | 4/2009 | Nord et al. | |
| 2009/0187422 | A1* | 7/2009 | Kaus | A61B 6/466 705/2 |
| 2009/0257657 | A1* | 10/2009 | Temmermans | G06T 3/0075 382/195 |
| 2009/0279739 | A1 | 11/2009 | Kaus et al. | |

FOREIGN PATENT DOCUMENTS

| | | |
|---|---|---|
| WO | 2007133932 A2 | 11/2007 |
| WO | 2009137652 A1 | 11/2009 |

OTHER PUBLICATIONS

Greve, Douglas N., and Bruce Fischl. "Accurate and robust brain image alignment using boundary-based registration." Neuroimage 48.1 (2009): 63-72.*

Kaus, Michael R., et al. "Assessment of a model-based deformable image registration approach for radiation therapy planning." International Journal of Radiation Oncology Biology Physics 68.2 (2007): 572-580.*

Mitsa, T., et al.; Image Registration Using Elastic Contours and Internal Landmarks; 1998; IEEE Trans. on Instrumentation and Measurement; pp. 451-455.

* cited by examiner

HYBRID POINT-BASED REGISTRATION

CROSS REFERENCE TO RELATED APPLICATIONS

This application is a national filing of PCT application Serial No. PCT/IB2012/052802, filed Jun. 4, 2012, published as WO 2012/172454 A1 on Dec. 20, 2012, which claims the benefit of U.S. provisional application Ser. No. 61/497,546 filed Jun. 16, 2011, which is incorporated herein by reference.

The present application relates generally to image registration. It finds particular application in conjunction with radiation therapy planning and will be described with particular reference thereto. However, it is to be understood that it also finds application in other usage scenarios and is not necessarily limited to the aforementioned application. For example, it finds application in certain image studies, computed tomography (CT) simulation, and so on.

Radiation therapy applies spatially targeted doses of radiation to target regions containing cancerous or malignant tissue. To precisely target radiation, radiation therapy is planned in advance based on images acquired of a target region. The target region, along with risk regions whose radiation dosage must be limited, are identified and delineated in the images. Further, radiation plan parameters, typically including a minimum or target dose to be delivered to the target regions, maximum permissible doses for the risk regions, and the like, are established. The identified regions and the radiation plan parameters serve as inputs to optimize radiation delivery.

Image registration provides an important tool for radiation therapy planning and certain image studies. Image registration seeks to find transformations and/or deformations that best align objects of interest (OOIs), such as regions of interest (ROIs) and points of interest (POIs), of a first image to a second image. Some applications include contour propagation; mapping positron emission tomography (PET) and/or CT images to a planning CT image; dose accumulation; and the like. It can be used for one or more adaptive planning events during the course of therapy; 4D planning and/or optimization; interfraction and/or intrafaction planning and/or optimization; composite planning; multimodality treatment plan generation; and the like.

There are many different variations of image registration that generally fall into two categories, image-based or point-based. Image-based approaches include algorithms such as optical flow (e.g., Demons), B-Splines, level sets, and so on and are driven by image intensity values. Point-based approaches are driven by corresponding points identified in each image and use interpolation or approximation to derive a registration map in between these points with algorithms, such as thin plate spline (TPS), elastic body spline (EBS), and so on.

The points for point-based approaches can be identified automatically through the use of interest point detection algorithms, such as salient point detection algorithms and/or corner and/or blob detection algorithms. Typically, the correspondence between interest points in the images is established through matching algorithms, such as a block-matching algorithm, a graph-matching algorithm, a feature descriptor matching algorithm, and so on. The points for point-based approaches can also be identified manually in the images. For example, corresponding anatomical landmarks can be manually identified in the images. The points for point-based approaches can also be identified manually and/or automatically through the use of meshes. Mesh models are fitted to the surfaces of corresponding structures in both images and corresponding mesh vertices are employed as points.

While the foregoing approaches each have their own strengths, they also have weaknesses. Automated interest point approaches rely on interest point detection algorithms to identify points and matching algorithms to establish a correspondence between points. However, in some cases, points cannot be identified and/or matched leading to local errors in the deformation mapping. Manual point approaches are tedious and not practical for clinical practice. Surface-mesh-vertex approaches are limited to points on the boundary of identified structures in the images.

The present application provides new and improved systems and methods which overcome the above-referenced problems and others.

In accordance with one aspect, a registration system for generating an image registration map is provided. The system includes one or more processors. The processors are programmed to receive a first image and a second image. Corresponding interest points in the first image and the second image are identified. Corresponding structures in the first image and the second image are identified. Corresponding boundary points of the structures in the first image and the second image are selected. A registration map is generated from the corresponding interest points and at least one pair of the corresponding boundary points.

In accordance with another aspect, a method for generating an image registration map is provided. A first image and a second image are received. Corresponding interest points in the first image and the second image are identified. Corresponding structures in the first image and the second image are identified. Corresponding boundary points of the structures are selected in the first and second images. A registration map from the corresponding interest points and at least one pair of the corresponding boundary points.

In accordance with another aspect, a method of therapy planning is provided. Corresponding interest points in the first image and the second image are identified and corresponding boundary points of structures in the first and second images are identified. The first image is adaptively registered to the second image based on a combination of one or more identified points and one or more identified boundary points.

One advantage resides in that points inside a structure and on a surface of the structure can be accurately identified.

Another advantage resides in the possibility of improved accuracy in registration map calculations.

Another advantage resides in reducing the need for manual point identification.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
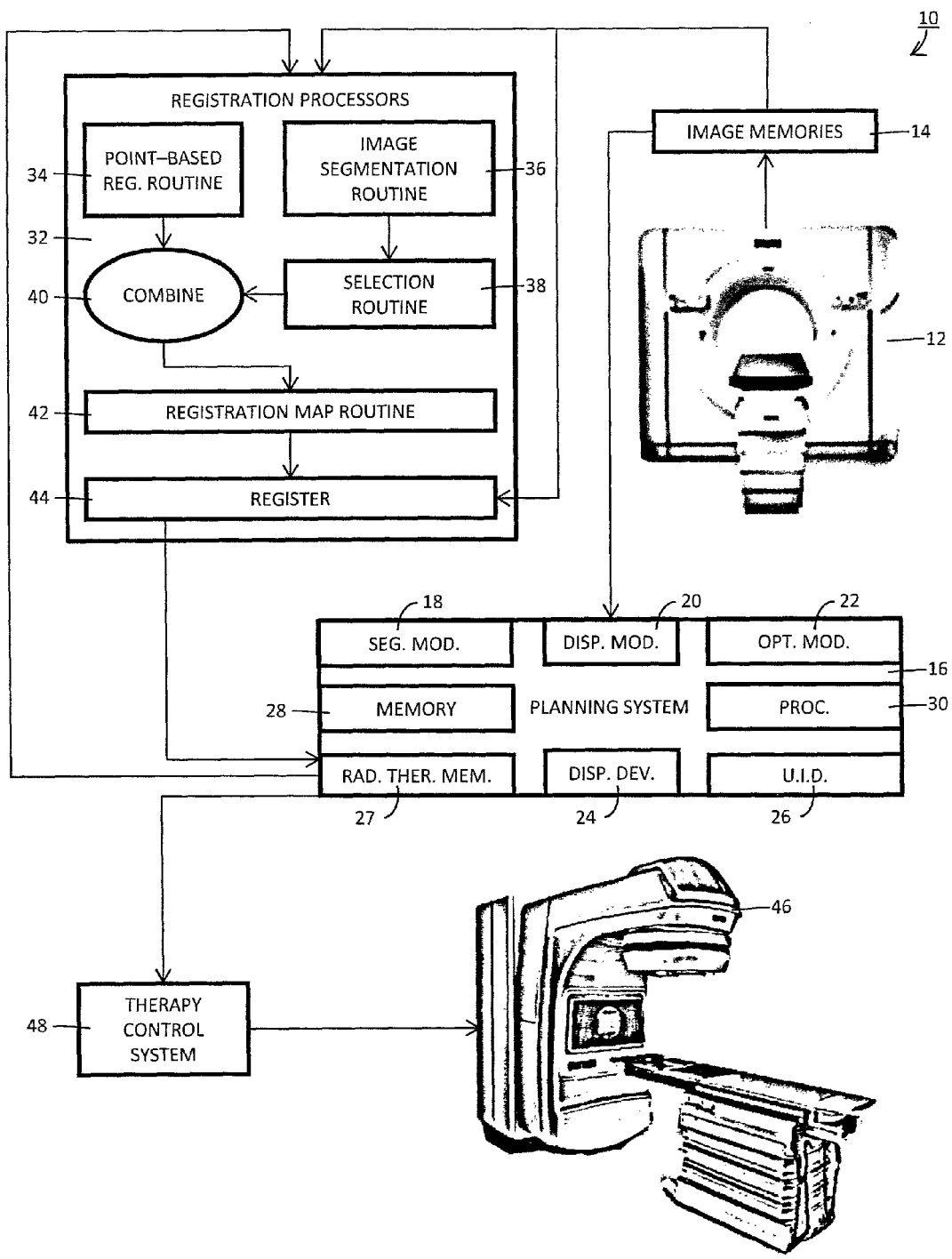
FIG. 1 is a block diagram of a radiation therapy system according to aspects of the present disclosure.

With reference to FIG. 1, a therapy system 10 includes one or more imaging modalities 12 for acquiring images of objects of interest (OOIs), such as regions of interest (ROIs) and points of interest (POIs), within patients. The imaging modalities 12 suitably include one or more of a computed tomography (CT) scanner, a positron emission tomography (PET) scanner, a magnetic resonance (MR) scanner, a single photon emission computed tomography (SPECT) scanner, a cone-beam computed tomography (CBCT) scanner, and the like. Images acquired from the imaging modalities 12 are stored in one or more image memories 14.

A planning system 16 of the therapy system 10 receives images of target regions for patients and employs the images for therapy planning. For example, the planning system 16 generates and/or updates treatment plans for patients using received images corresponding to the patients. Typically, the images are received from the imaging modalities 12 via the image memories 14, but other sources are contemplated. To facilitate therapy planning, the planning system 16 includes a segmentation module 18, a display module 20, an optimization module 22, and the like.

The segmentation module 18 identifies and delineates between regions, such as target regions and risk regions, in received images. Such regions are typically delineated by contours surrounding the regions. Identification and delineation can be performed manually and/or automatically. As to the former, the segmentation module 18 cooperates with the display module 20 to allow clinicians to manually identify and delineate between the regions. As to the latter, a segmentation algorithm, such as hierarchical clustering algorithm, random walks algorithm, and so on, is employed.

The display module 20 allows clinicians to at least one of generate, modify and view contours. In that regard, the display module 20 displays images and, in some embodiments, corresponding contours on a display device 24. Clinicians can then generate and/or modify contours on the images using one or more user input devices 26. Additionally or alternatively, the display module 20 allows clinicians to enter and/or define plan parameters for contoured regions.

The optimization module 22 receives as input at least contours and plan parameters, typically generated by the segmentation module 18 and/or the display module 20. The optimization module 22 optionally receives other relevant inputs, such as an attenuation map indicative of radiation absorption. Based on the inputs, the optimization module 22 generates a therapy plan complying with the plan parameters and any other relevant inputs. Therapy plans generated by the optimization module 22 are suitably stored in one or more therapy memories 27.

The planning system 16 includes one or more memories 28 and one or more processors 30. The memories 28 store executable instructions for carrying out the functions associated with the planning system 16, including those associated with the segmentation module 18, the display module 20, and the optimization module 22. The processors 30 execute the executable instructions stored on the memories 28. In certain embodiments, the planning system 16 further includes a communication unit for communication with, for example, the image memories 14 via a communications network and/or a data bus, such as a local area network or the Internet.

To facilitate therapy planning across therapy sessions and/or across a plurality of images, one or more registration processors 32 generate a registration map between a first image and a second image using a plurality of point identification methods, as described in detail below in connection with FIG. 2. In that regard, the registration processors 32 suitably execute computer executable instructions embodying the method 50 of FIG. 2 on one or more memories, such as the memories 28 of the planning system 16. The first image is suitably a new image acquired from the imaging modalities 12, via, for example, the image memories 14, and the second image is suitably an image previously used to generate and/or update a treatment plan, optionally obtained from the therapy memories 27. The point identification methods include a method of identifying corresponding interest points in the images and a method of identifying corresponding boundary points in the images. Other point identification methods can additionally or alternatively be employed.

When generating the registration map, a point-based registration routine 34 identifies corresponding interest points in the first image and the second image. One challenge, however, is that when performing point-based registration there can be surface or other areas with no or a dearth of identifiable points, which can lead to a lack of accuracy in the area of sparse point density. Therefore, an image segmentation routine 36 is employed. The image segmentation routine 36 identifies corresponding structures in the first image and the second image. Further, the image registration routine identifies corresponding boundary points on the first image and the second image. In some embodiments, boundary points are identified by fitting mesh models to the identified structures, such as tumors or organs, in the first image and the second image and employing corresponding mesh vertices as boundary points. For example, a surface model can be fitted to a structure using grey scale values in the image. As another example, a mesh model can be fitted to a structure using interactive delineation by a clinician. In other embodiments, boundary points are identified as the centers of corresponding boundary voxels of binary mask representations of the regions of interest (ROIs). After identifying corresponding boundary point points, the result is typically a very large number of corresponding boundary points, some of which are in the area the point-based registration had the dearth of identified points. These corresponding boundary points can be employed as interest points.

A point selection routine 38 selects at least some of the boundary points for addition to the interest points. In some embodiments, because the image-based registration creates such a large number of boundary points, only a subset of the boundary points are selected. Various techniques or criteria for limiting the number of points are contemplated. For example, the subset can be limited to points in or near the area with a dearth of points, points deemed to be more reliable, points in regions with more irregular surface characteristics, a predetermined number of randomly selected points, and the like.

After selecting the boundary points, the selected boundary points are combined 40 with the interest points, in which step some conflicting or unnecessary interest points may be discarded, and a registration map routine 42 uses an appropriate algorithm, such as a thin plate spline algorithm, an elastic body spline algorithm, or the like, to generate a registration map. In some embodiments, a registration routine 44 registers the first image to the second image using the registration map. The registered image can be used for, for example, directly comparing the first image to the second image in a fusion display, dose accumulation, adaptive planning, updating a treatment plan, and so on. As illustrated, the registered image is employed to update a treatment plan in the therapy memories 27.

At a scheduled day and time for a therapy session of a patient, a therapy delivery apparatus 46 delivers a therapy to the patient. The therapy can include radiation therapy involving x-rays, protons, high-intensity focused ultrasound (HIFU), and the like, ablation therapy, brachytherapy, and so on. Suitably, the therapy delivery apparatus 46 is controlled by a therapy control system 48 in accordance with a therapy plan. The therapy plan can be received from, for example, the therapy memories 27.

Figure 2:
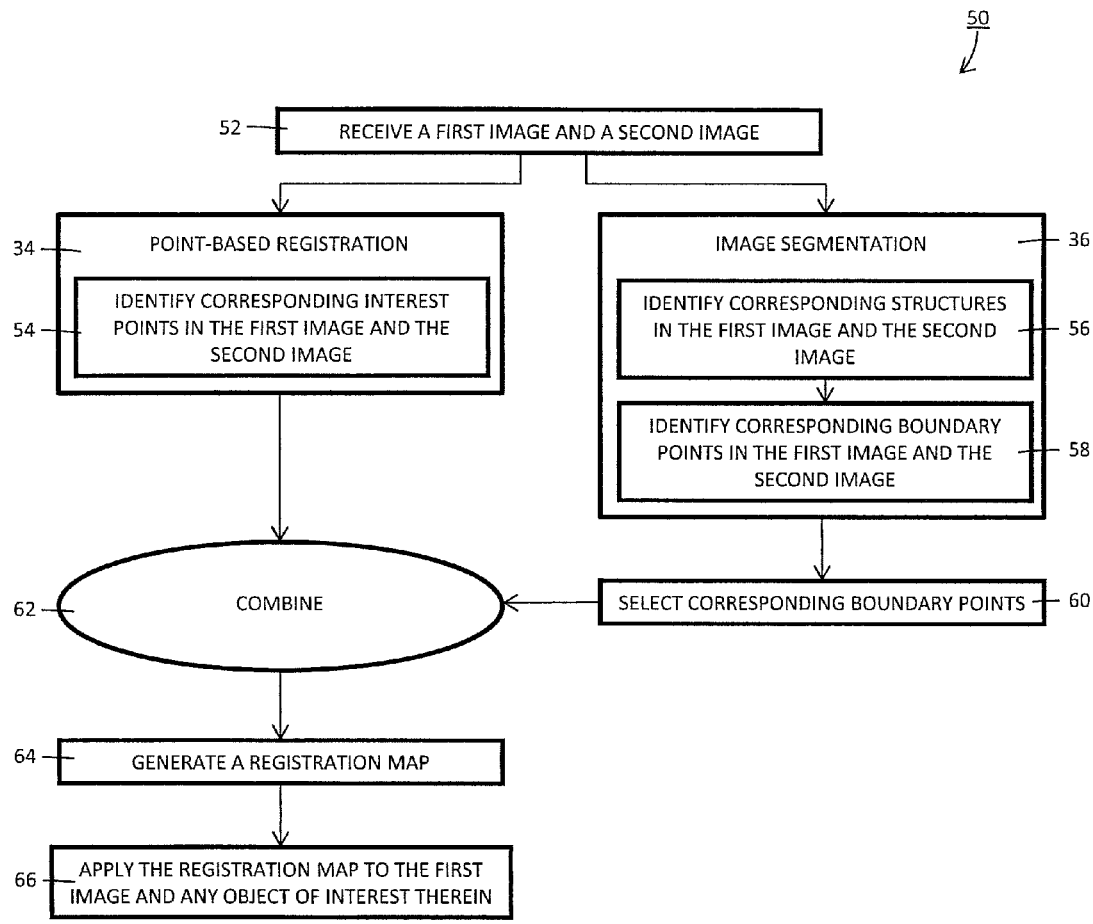
FIG. 2 is a block diagram of a method performed by a hybrid point-based registration module according to aspects of the present disclosure.

With reference to FIG. 2, a method 50 for generating a registration map, suitably performed by the registration processors 32, includes receiving 52 a first image and a second image. Typically, the images are received from at least one of the image memories 14 and the therapy memories 27, but it is contemplated that the images are received from other sources, such as a central records storage system for patients. Further, the images are suitably focused on the same object of interest, such as an organ or tumor.

Corresponding interest points in the first image and the second image are manually and/or automatically identified 54 using the point-based registration routine 34. For example, one or more interest points are identified in the first image, and corresponding interest points are identified in the second image. As to manual identification, one or more user input devices, such as the user input devices 26 of the planning system 16, and/or a display device, such as the display device 24 of the planning system 16, are employed to allow a clinician to manually identify corresponding interest points. For example, a clinician can manually identify corresponding interest points for clear anatomical landmarks in the first image and the second image. As to automatic identification, an interest point detection algorithm, such as a salient point detection algorithm or a corner and/or blob detection algorithm, is employed, where the correspondence between the interest points in the first image and the second image is suitably established using a matching algorithm, such as a block-matching algorithm, a graph-matching algorithm, a feature descriptor matching algorithm, and so on.

Corresponding structures in the first image and the second image are manually and/or automatically identified 56 using the image segmentation routine 36. A structure includes, for example, an organ, a tumor, or other regions. Suitably, the structures are identified in at least one of regions of the images where the density or distribution of identified interest points is below a threshold, typically representative of a low density or distribution of identified points (e.g., because there are limited interest points, points with significant matching error, or other reasons), and regions of the images that have boundary contrast exceeding a threshold, typically representative of a good boundary contrast (implying a reliable segmentation accuracy). For manual identification, one or more user input devices, such as the user input devices 26 of the planning system 16, and/or a display device, such as the display device 24 of the planning system 16, are employed to allow a clinician to manually identify corresponding structures.

Corresponding boundary points of the identified 58 structures are then identified in the first image and the second image. In some embodiments, this is performed using mesh models, where mesh models are fitted to the surfaces of each pair of corresponding structures in the images to create mesh pairs with corresponding mesh vertices using the image segmentation routine 36. For example, a mesh model is fitted to a structure in the first image, and an identical mesh model is fitted to a corresponding structure in the second image. The corresponding mesh vertices are then employed as boundary points. The meshes are typically formed from polygons, such as triangles. So as to ensure the meshes for corresponding structures are equivalently oriented in the images while being fitted, the identical meshes can be oriented relative to corresponding anchor points in the images. Anchor points can be identified manually and/or automatically and, in certain embodiments, include corresponding interest points from the point based registration routine 32 proximate the structure. Other approaches to orienting the mesh are, however, contemplated.

Once the image-based registration of the pair of images is complete, corresponding pairs of boundary points from the corresponding structures are selected 60 as additional interest points, preferably intelligently to reduce computation time. For example, the corresponding pairs of boundary points are limited to vertice pairs representing the extent of the structures in regions sparsely populated by interest points from the point based registration routine 32. It is contemplated that the corresponding pairs of boundary points are limited manually and/or automatically. As to the latter, a thinning algorithm can be employed. The thinning algorithm can, for example, limit the boundary points to boundary points in or near the area with the dearth of points, boundary points deemed to be more reliable, boundary points in regions with more irregular surface characteristics, a predetermined number of randomly selected boundary points, and the like.

The selected boundary points (interest points) are combined 62 with the identified interest points from the point based registration routine 32. In some embodiments, the identified interest points combined with the selected boundary points are limited to the most reliable pairs of interest point. For example, the interest points more separate or remote from sparsely populated areas are combined with the selected boundary points. Additionally or alternatively, in some embodiments, the combined point pairs are weighted with selected boundary points weighted less heavily than the interest points. The weight suitably indicates a reliability of the correspondence.

The identified interest points are employed to generate 64 a registration map using a registration algorithm, such as TPS, EBS, and so on. The registration algorithm identifies the transformations and/or deformations that best align the interest points of the first image to the corresponding interest points of the second image. In embodiments where the points are weighted, highly weighted points influence the identified transformations and/or deformations more so than lesser weighted points. Advantageously, the registration map allows points identified in the coordinate frame of the first image to be mapped to the coordinate frame of the second image. For example, a contour defined in the coordinate frame of a new diagnostic image can be mapped to the coordinate frame of a radiotherapy planning image using the registration map.

Once the registration map is generated, the registration map can be applied 66 to the first image to register the first image to the second image. That is to say, the first image can be mapped to the coordinate frame of the second image to yield a registered image. The registration map can also be applied to propagate any object of interest (OOI) from the first to the second image. The registered image can be used for, for example, directly comparing the first image to the second image, dose accumulation, adaptive planning, updating a treatment plan, and so on. In certain embodiments, at least one of the first image, the second image, and the registered image are displayed on a display device, such as the display device 24 of the planning system 16.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A therapy-planning system comprising:
   a planning system configured to generate a therapy plan for delivery of therapy to a target region of a patient using a first image received from at least one imaging modality;
   a therapy delivery apparatus configured to deliver the therapy to the target region;
   one or more registration processors programmed to:
      receive the first image and a second image received from at least one imaging modality,
      identify corresponding interest points in the first image and the second image,
      identify corresponding structures in the first image and the second image,
      identify boundaries of the identified corresponding structures,
      fit corresponding mesh models to the identified boundaries of the corresponding structures of the first image and the second image in one or more regions in which a density of corresponding interest points is below a threshold,
      select corresponding vertices of the mesh models in the first image and the second image as the corresponding boundary points,
      generate a registration map from the corresponding interest points and a plurality of the corresponding boundary points using point based registration;
   wherein the planning system is further configured to update the therapy plan based on the registration map; and
   a therapy control system configured to control the therapy delivery system to deliver the therapy in accordance with the updated therapy plan.

2. The system according to claim 1, wherein the registration map is generated using thin plate spline and/or elastic body spline.

3. The system according to claim 1, further including:
   at least one diagnostic imaging system configured to scan the patient and reconstruct diagnostic images including the first and second images.

4. The system according to claim 1, wherein the one or more registration processors are further programmed to:
   weight the interest points and the boundary points used in the registration map generation based on reliability.

5. The system according to claim 4, wherein the one or more registration processors are further programmed to:
   apply the registration map to the first image to register the first image to the second image.

6. The system according claim 1, wherein the at least one imaging modality includes at least one of: a computed tomography (CT) scanner, a positron emission tomography (PET) scanner, a magnetic resonance (MR) scanner, a cone-beam computed tomography (CBCT) scanner, and a single photon emission computed tomography (SPECT) scanner.

7. The therapy planning system according to claim 1, wherein the therapy includes at least one of radiation therapy, ablation therapy, and brachytherapy.

8. A method of therapy delivery comprising:
   with one or more processors, reconstructing first diagnostic image data generated by a first diagnostic scanner into a planning image;
   with the one or more processors, generating a therapy plan for delivery of therapy to a patient from the planning image;
   storing the planning image in a memory;
   with the one or more processors, reconstructing second diagnostic image data generated by a second diagnostic scanner subsequent to generation of the therapy plan into a second diagnostic image;
   with the one or more processors, identifying corresponding interest points in the planning image and the second image;
   with the one or more processors, segmenting the planning image and the second image in common regions of the planning and second images where a density of the identified corresponding interest points is below a threshold to generate corresponding boundaries of corresponding structures;
   with the one or more processors, identifying corresponding boundary points of the corresponding boundaries;
   with the one or more processors, generating a registration map from a combination of identified interest points and one or more identified boundary points;
   with the one or more processors, updating the radiation therapy plan based on the registration map;
   with the one or more processors, controlling a therapy delivery device to deliver the therapy according to the updated therapy plan.

9. The method according to claim 8, wherein:
   segmenting the planning image and the second image includes fitting mesh models to the corresponding boundaries of the first image and the second image; and,
   generating the registration map includes selecting corresponding vertices of the mesh models in the planning image and the second image as the boundary points.

10. The method according to claim 8, further including:
    applying the registration map to the first image to register the first image to the second image; and,
    displaying at least one of the first image, the second image, and the registered image on a display device.

11. A system comprising:
    one or more processors configured to:
       receive a first diagnostic image and a second diagnostic image of a common anatomical region of a patient;
       identify corresponding points of interest in the first diagnostic image and the second image;
       identify common structures in the first diagnostic image and the second diagnostic image;
       segment the common structures by fitting corresponding mesh models to the common structures of the first diagnostic image and the second diagnostic image;

select corresponding vertices of the mesh models in the first diagnostic image and the second diagnostic image as a set of boundary points;

select a subset of the corresponding vertices in one or more regions where a density of the identified interest points is below a threshold;

weight the selected interest points and the subset of the selected vertices based on reliability;

generate a registration map based on the weighted image points and the weighted vertices;

register the first and second diagnostic images with the registration map; and a display device configured to display at least one of the registered first and second images.

12. The system according to claim 11, wherein the one or more processors are further configured to:
update a first therapy treatment plan with the registration map.

13. The system according to claim 12, further including:
a therapy delivery device; and
wherein the one or more processors are further configured to control the therapy delivery device to deliver therapy according to the updated treatment plan.

14. The system according to claim 11, wherein the one or more processors are further configured to:
apply a plate spline and/or an electric body spline to generate the registration map.

15. The system according to claim 11, further including:
a planning system configured to generate a first treatment plan based on the first diagnostic image.

16. The system according to claim 15, wherein the one or more processors are configured to:
transform the first treatment plan with the registration map to generate an updated treatment plan.

17. The system according to claim 16, further including:
a radiation therapy device configured to deliver radiation to the patient under control of the one or more processors; and
wherein the one or more processors are further configured to control the radiation therapy device to deliver radiation to the patient as indicated by the updated treatment plan.

18. The system according to claim 16, further including:
a therapy treatment device configured to deliver therapy to the patient according to the updated treatment plan.

19. The system according to claim 15, further including:
a first diagnostic imaging scanner configured to generate the first diagnostic image prior to the planning system generating the first treatment plan;
a second diagnostic imaging scanner different from the first diagnostic imaging scanner configured to generate the second diagnostic image subsequent to the planning system generating the first treatment plan.

* * * * *